United States Patent
Cresens et al.

(10) Patent No.: US 10,345,454 B2
(45) Date of Patent: Jul. 9, 2019

(54) METHOD FOR RESHAPING THE CHARACTERISTIC EXPOSURE RESPONSE AND DOSIMETRY OF A DIRECT RADIOGRAPHY SYSTEM

(71) Applicant: AGFA NV, Mortsel (BE)

(72) Inventors: Marc Cresens, Mortsel (BE); Stefan Stommels, Mortsel (BE)

(73) Assignee: AGFA NV, Mortsel (BE)

( * ) Notice: Subject to any disclaimer, the term of this patent is extended or adjusted under 35 U.S.C. 154(b) by 0 days.

(21) Appl. No.: 15/769,075

(22) PCT Filed: Oct. 18, 2016

(86) PCT No.: PCT/EP2016/074929
§ 371 (c)(1),
(2) Date: Apr. 18, 2018

(87) PCT Pub. No.: WO2017/067902
PCT Pub. Date: Apr. 27, 2017

(65) Prior Publication Data
US 2018/0299565 A1 Oct. 18, 2018

(30) Foreign Application Priority Data
Oct. 21, 2015 (EP) .................... 15190697

(51) Int. Cl.
*G01T 1/164* (2006.01)
*G01T 1/24* (2006.01)
*H05G 1/26* (2006.01)
*A61B 6/00* (2006.01)
*G01T 1/02* (2006.01)

(52) U.S. Cl.
CPC ............ *G01T 1/1645* (2013.01); *A61B 6/582* (2013.01); *G01T 1/02* (2013.01); *G01T 1/24* (2013.01); *H05G 1/265* (2013.01)

(58) Field of Classification Search
CPC ........... G01T 1/02; G01T 1/1645; G01T 1/24; H05G 1/265; A61B 6/582
See application file for complete search history.

(56) References Cited

U.S. PATENT DOCUMENTS

2010/0142791 A1  6/2010  Tsuji

OTHER PUBLICATIONS

Official Communication issued in International Patent Application No. PCT/EP2016/074929, dated Dec. 6, 2016.
Seibert et al., "Flat-field correction technique for digital detectors", Optomechatronic Micro/Nano Devices and Components III, vol. 3336, Jan. 1, 1998, pp. 348-354.
(Continued)

*Primary Examiner* — Mark R Gaworecki
(74) *Attorney, Agent, or Firm* — Keating and Bennett, LLP

(57) ABSTRACT

A method for reshaping the characteristic exposure response and dosimetry of a direct radiography system into a specified exposure response profile includes pixel-wise converting image data according to a response transfer model which is derived from an x-ray generator's post exposure parameters data associated with image signals obtained at various exposure levels during system calibration and from a few extra dose measurements and their corresponding post exposure data also gathered during system calibration under reference exposure conditions.

7 Claims, 6 Drawing Sheets

(56) References Cited

OTHER PUBLICATIONS

Wang et al., "Comprehensive and automated image quality performance measurement of computed radiography systems", Optomechatronic Micro/Nano Devices and Components III, vol. 4320, Feb. 18, 2001, pp. 308-315.

Cooper et al., "Evaluation of detector dynamic range in the x-ray exposure domain in mammography: A comparison between film-screen and flat panel detector systems", Medical Physics, vol. 30, No. 10, Oct. 1, 2003, pp. 2614-2621.

Winkler et al., "Dose-response characteristics of an amorphous silicon EPID", Medical Physics, vol. 32, No. 10, Sep. 21, 2005, pp. 3095-3105.

METHOD FOR RESHAPING THE CHARACTERISTIC EXPOSURE RESPONSE AND DOSIMETRY OF A DIRECT RADIOGRAPHY SYSTEM

CROSS REFERENCE TO RELATED APPLICATIONS

This application is a 371 National Stage Application of PCT/EP2016/074929, filed Oct. 18, 2016. This application claims the benefit of European Application No. 15190697.1, filed Oct. 21, 2015, which is incorporated by reference herein in its entirety.

BACKGROUND OF THE INVENTION

1. Field of the Invention

The present invention relates to direct radiography. The invention more particularly relates to a method for reshaping the characteristic exposure response of a flat-panel detector system based on post exposure parameter feedback from an x-ray generator and on a few additional dose measurement performed under reference conditions during system calibration.

2. Description of the Related Art

System calibration is extremely important in direct radiography where solid-state array-sensor detectors are used to acquire digital images for diagnostic or inspection purposes in various clinical, veterinary or industrial applications.

These image acquisition devices are composed of complex, densely integrated and highly interacting electro-optical and electronic systems each having their typical tolerances, physical properties variability and inevitable local defects.

The overall image quality performance of a radiographic system can also depend on the ambient temperature, the humidity, the atmospheric pressure as well as on the x-ray exposure history linked to the degree of system usage and the system's actual age.

In addition gradually increasing levels of system contamination due to the external contact of the system components with radiographed patients, animals, objects, operator personnel or caused by fiber- and dust particle pollution can depend on the equipment's application-specific usage modes and the ambient climate conditions and can influence the properties and the behaviour of the system's individual components and processes thus leading to more frequent, beyond the periodically scheduled, cleaning and recalibration activities.

Given that next to the pixel-individual light-trapping or direct x-ray detection array-circuitry also massive amounts of highly miniaturized pixel-, row-, and column-specific galvanic interconnections and several block-wise arranged read-out electronic circuits should cooperate harmonically, it can be understood that the signal-quality and the x-ray exposure response of the corrected panel image might degrade with usage time.

Therefore the direct radiography image-acquisition system needs to be cleaned and recalibrated on a regular basis.

These necessary activities are typically executed not only after shipment and installation of the equipment as a precondition to performing an initial acceptance test but also before each scheduled periodic quality control test.

After moving the equipment, after system modifications and after preventive maintenance or repair interventions to critical system-components an additional system recalibration is often necessary as well to ensure a safe and effective operation of the system within the predetermined overall image quality range.

This calibration process not only delivers a better adjusted and cleaner state of the radiographic equipment but also generates one or multiple image-wide maps at pixel resolution for the reconstruction of unstable and or defective pixels, rows and columns in addition to one or more gain maps for the software- or hardware-based, pixel-wise sensitivity-correction of raw diagnostic images.

Besides these relative sensitivity corrections at pixel level to ensure a smooth image at any even exposure level also the system's absolute sensitivity to x-rays and the characteristic shape of its corrected image data response to exposure are extremely important as well.

For image metrics on the signal and on the noise power spectra for image quality control purposes the panel's corrected image data should comply to specified dosimetric requirements.

These link the image data range in an absolute way to x-ray exposure levels by assigning absorbed dose limits and associated tolerances to the upper extremity of the system's operational range.

Image processing software for improved visualisation imposes the expected profile of the system's characteristic exposure response to ensure that the contrast enhanced image is represented correctly over the often vast range of image-wise distributed local exposure levels which is typical for x-ray projected shadow imagery.

SUMMARY OF THE INVENTION

One aspect of this invention is to conceive a method for reshaping the measured characteristic exposure response and the dosimetry of a direct radiography system into a specified exposure response profile based on post exposure parameter data from the x-ray generator.

Another aspect is to optimize this method such that a minimal amount of additional dose measurements and associated post exposure generator data, both obtained under reference exposure conditions during system calibration, are required to minimize the system's down time.

A further aspect relates to such a method whereby the time required to convert a newly acquired image into a a corrected image according to the specified characteristic exposure response is reduced.

Still further aspects will become apparent from the description given hereinafter.

The above-mentioned aspects are obviated by a method having the specific steps set out below.

Specific features for preferred embodiments of the invention are also set out below.

Further advantages and embodiments of the present invention will become apparent from the following description and drawings.

DETAILED DESCRIPTION OF THE PREFERRED EMBODIMENTS

Upon an initial calibration after installation or while performing a periodic or an additional re-calibration of a flat panel detector direct radiography system, the use of this equipment for diagnostic or inspection imaging purposes is temporarily suspended.

Time and personnel are freed up to perform measurements and acquire new calibration-dedicated image sets, composed of non-exposed as well as homogeneously exposed raw flat panel detector images, in order to update the various defective pixel maps, the gain maps and the characteristic exposure response transfer function necessary to correct the many thousands of raw diagnostic images according to the imposed dosimetry and the exposure response profile specifications.

Below a specific embodiment of the method for reshaping the measured characteristic exposure response of a direct radiography system into a specified response profile is explained.

Said embodiment uses the x-ray generator's post exposure parameter data associated with each newly acquired image in combination with background knowledge extracted from additional dose measurement and their associated post exposure parameter data obtained under reference exposure conditions during system calibration.

Figure 1:
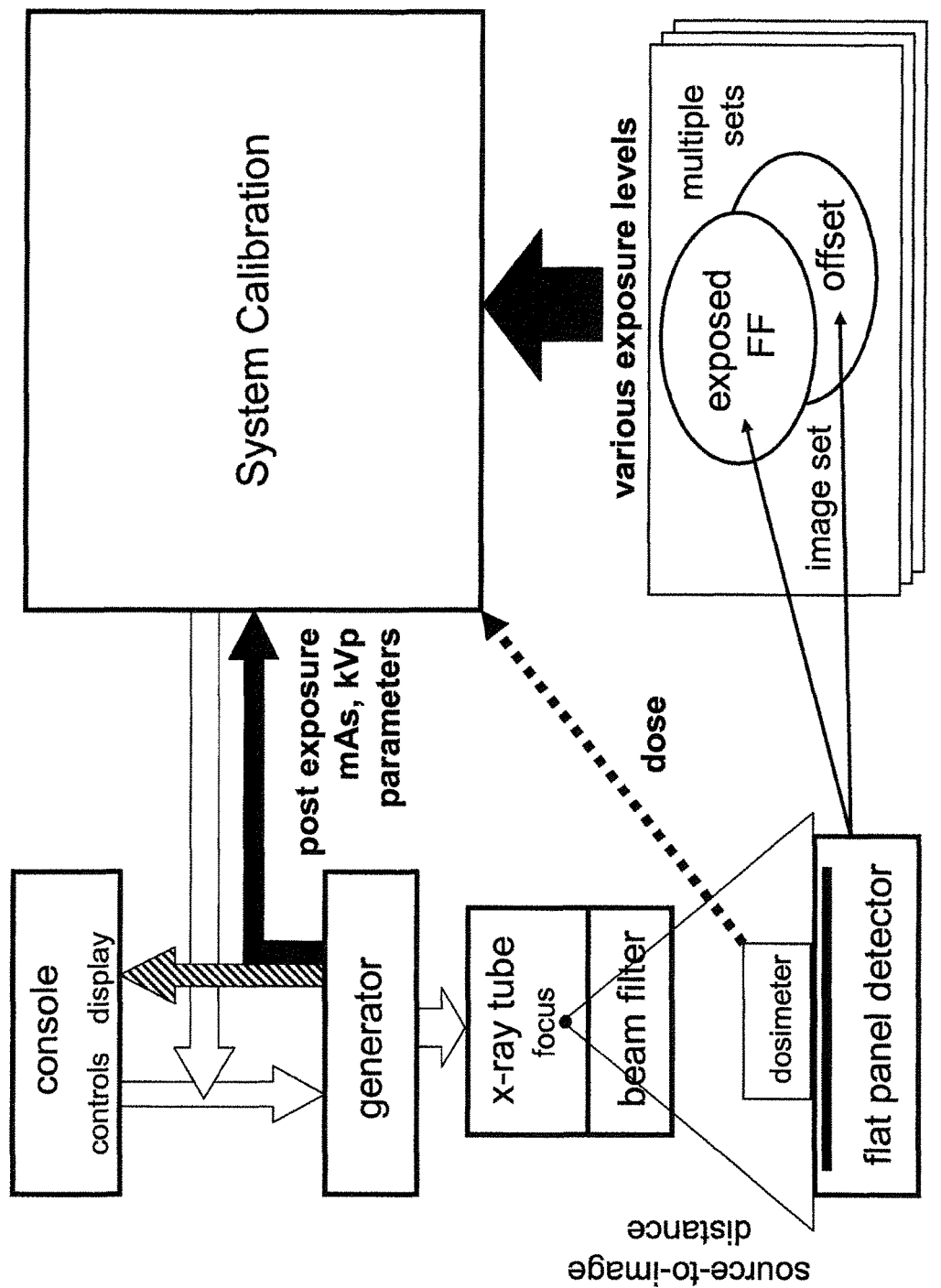
FIG. 1 represents the various interconnected components of the direct radiography system during system calibration.

FIG. 1 shows a block-schematic diagram of the interconnections between the various direct radiography system components as configured during system calibration.

In the preparatory phase before initial acceptance testing or during recalibration prior to periodic quality control the flat panel's array-sensor must be subjected to evenly distributed amounts of impinging x-ray radiation across its entire entry surface.

Not only the homogeneity or evenness of this x-ray field to which the solid-state detector is exposed is important.

Also the absolute, time-integrated intensity of the radiation field must be set such that a wide range of specified exposure levels can be achieved by modifying the system's pre-exposure parameters.

The x-ray generator translates the various pre-exposure parameters including the x-ray tube voltage and the current-time-product it receives from the manual console controls of from the automatic calibration support system into the right electrical signals and timing to drive the x-ray tube assembly.

The x-ray tube converts a fraction of the electrical energy package it receives from the generator into x-ray radiation which is emitted towards the flat panel detector.

These x-rays are partially absorbed by the beam filter which controls the beam's energy spectrum and are spatially diverged while crossing the source-to-image distance between the tube's selected focal point and the location of the array-sensor which captures the projected shadow image.

Several system parameters have an impact on the end resulting exposure level at the surface of the flat panel detector.

The time-integrated x-ray energy package which is absorbed by the detector and converted into a captured image grows with increasing tube voltage and current-time-product parameter settings towards the x-ray generator.

Decreasing the beam filter absorption and reducing the source-to-image distance result in a higher exposure level at the flat panel detector.

A dosimeter, centrally positioned on top of the panel's input face, is used to measure the end resulting exposure level expressed as a certain amount of absorbed x-ray dose.

A first exposure of the dose-meter within the predetermined calibration reference target range can be made quickly by selecting the prescribed pre-exposure parameters for that geometry and system configuration on the x-ray generator before the actual exposure is made.

After exposure the dosimeter displays the dose it absorbed for that shot-specific exposure level and this value is entered for system calibration purposes.

The generator also outputs its shot-specific post exposure data including the accurately measured tube voltage and the accurately measured current-time-product which drove the x-ray tube to generate that specific exposure.

This post exposure generator data is fed automatically into the calibration support system.

Due to the tolerances and the variability of the high tension and current generating circuits inside the generator, these post-exposure parameters data more closely represent the actual drive state of the x-ray tube than the often much coarser pre-exposure parameters set by the console or the calibration system prior to exposure.

By consequence the post-exposure parameters are also more representative for the shot-specific measured dose than the pre-exposure parameters which show a weaker correlation with the absorbed dose readings.

In the same way a second reference exposure with an identical pre-exposure current-time-product setting but with a 1 kV increased tube voltage is made to determine the sensitivity of the exposure level to tube voltage as will be explained in FIG. 3.

The measured dose for this second exposure at elevated tube voltage is entered manually for system calibration purposes along with its automatically associated shot-specific post exposure parameters data from the generator.

Next the dosimeter is removed from flat panel detector and the regular sequence of calibration activities starts.

This process includes the acquisition of multiple sets of evenly exposed (flatfield) images at various exposure levels along with their time-associated unexposed (offset) images.

Each time an exposure is made and the corresponding flatfield image is acquired the generator's shot-specific post exposure parameters are automatically entered into the calibration support system.

These flatfield image sets at various exposure levels are acquired at the same calibration reference tube voltage as used during the first dosimeter exposure.

Slight differences in the actual tube voltage as accurately measured and indicated by generator's post exposure parameters will occur due to shot-to-shot tolerances in the high tension generation circuitry and these are taken into account.

Figure 2:
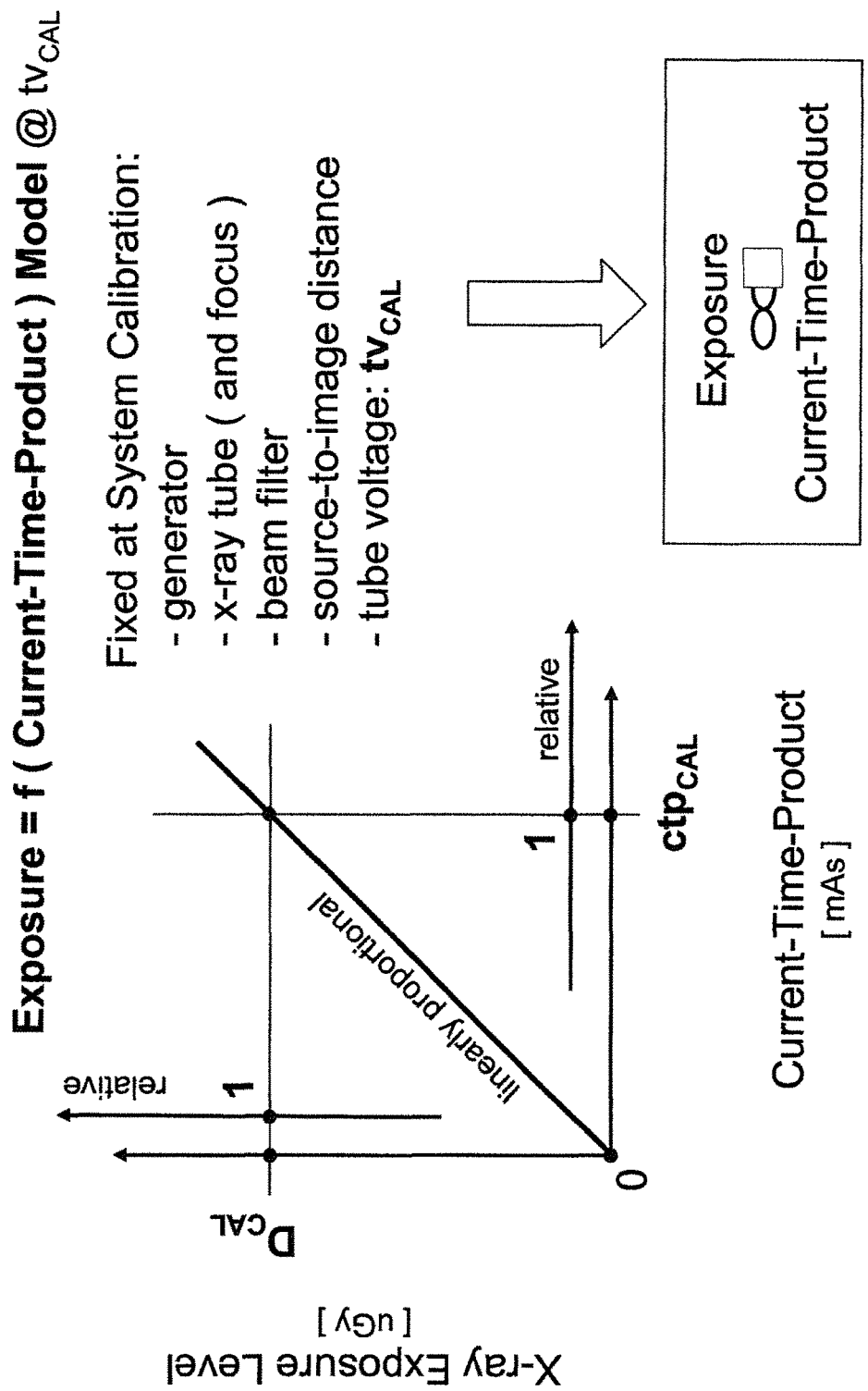
FIG. 2 shows the exposure level profile as a function of the x-ray tube's current-time-product under fixed tube voltage conditions.

FIG. 2 shows the exposure level profile as a function of the x-ray tube's current-time-product under fixed tube voltage conditions.

The exposure level at the entry surface of the flat panel detector will be linearly proportional to the current-time-product at which the x-ray tube was driven during the exposure if no changes to the x-ray system's configuration and projection geometry are made meaning that the same generator, tube and focal point, beam filter, source-to-image distance and tube voltage are used.

The dosimeter, positioned on top of the flat panel detector, measures the shot-specific absorbed calibration reference dose $D_{CAL}$ and this dose reading is entered after the first exposure.

The generator's associated post exposure parameters data including the shot-specific calibration reference current-time-product $ctp_{CAL}$ is fed automatically into the calibration support system.

Figure 3:
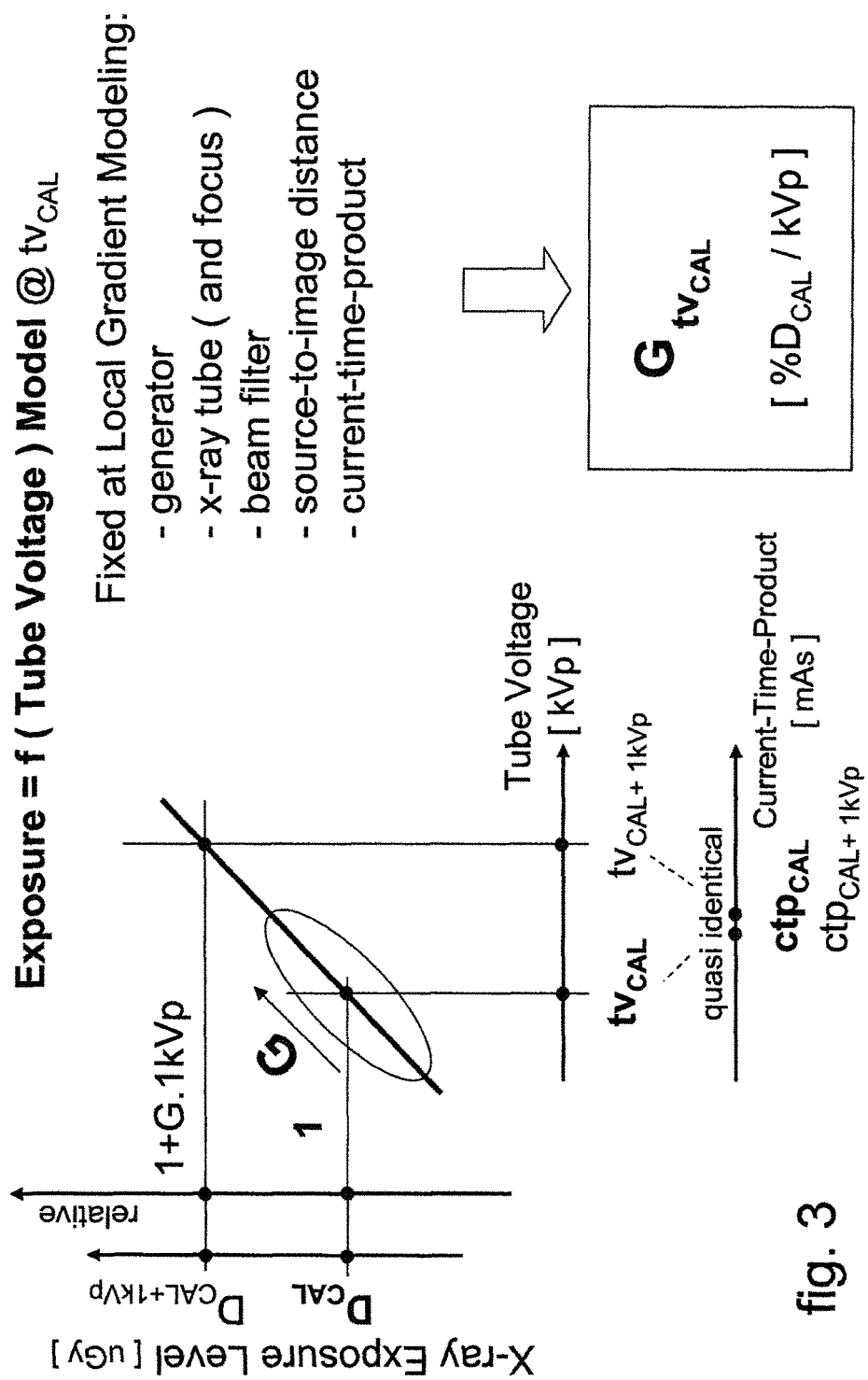
FIG. 3 shows the exposure level profile as a function of the x-ray system's tube voltage under fixed current-time-product conditions.

FIG. 3 shows the exposure level profile as a function of the x-ray system's tube voltage under fixed current-time-product conditions.

The pre-exposure current-time-product setting to the generator is identical but the tube-voltage setting is increased with 1 kV for the second calibration exposure of the dosimeter.

After this exposure at elevated tube voltage the dosimeter reading $D_{CAL+1kVp}$ is entered along with it's corresponding post exposure tube voltage parameter $tv_{CAL+1kVp}$ which was accurately measured and automatically entered by the generator.

Due to inevitable shot-to-shot tolerances in the constant current regulation circuitry during exposure, a slight difference between the values of the post exposure current-time-product parameter values, which were accurately measured internally by the generator itself, will always exist for an identical pre-exposure current-time-product setting as seen from the figure.

A local model of the exposure sensitivity to tube voltage changes near the calibration reference tube voltage $tv_{CAL}$ can be extracted based on the first and the second dose measurements and their corresponding post exposure parameters measured by the generator.

The local gradient of this model's profile at the calibration voltage is calculated as:

$$G_{tvCAL} = \frac{D_{CAL+1kVp} - D_{CAL}}{tv_{CAL+1kVp} - tv_{CAL}} \cdot \frac{ctp_{CAL}}{ctp_{CAL+1kVp}}$$

This formula compensates for the inevitable slight difference in the post exposure current-time-product parameter between the first and the second dosimeter exposures by using a correction factor which is determined by relying on the proportionality of the exposure level with the current-time-product and on the knowledge of both quasi identical ctp-values.

Figure 4:
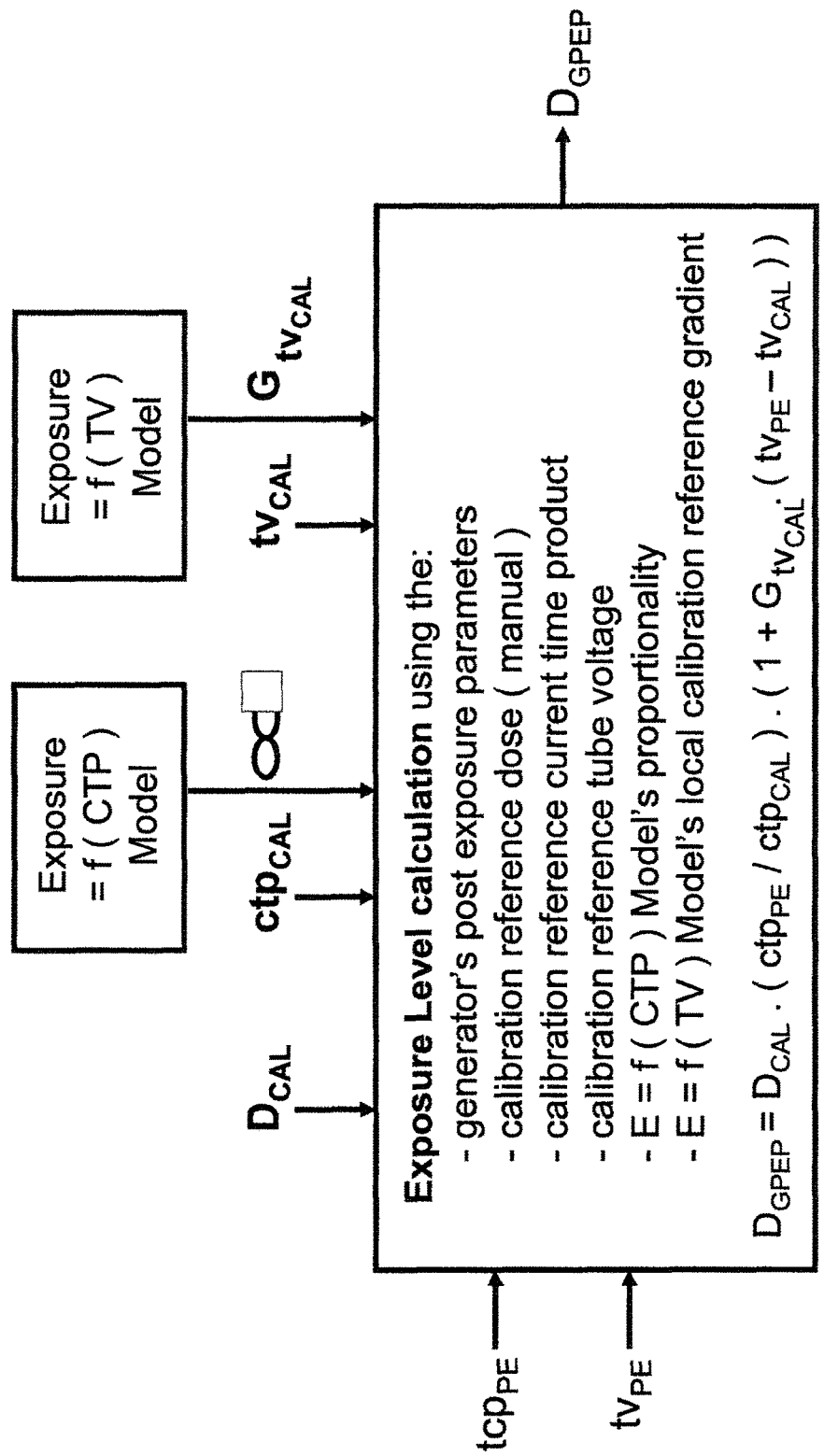
FIG. 4 explains how the post exposure parameter dose of an image is calculated from the various input data and model derived parameters.

FIG. 4 explains how the generator's post exposure parameter based dose $D_{GPEP}$ of a freshly acquired image at a tube voltage $tv_{PE}$ near $tv_{CAL}$ is calculated by combining the calibration dose reading $D_{CAL}$ and it's shot-specific post exposure parameters: $ctp_{CAL}$ and $tv_{CAL}$ with the post exposure parameter data: $tcp_{PE}$ and $tv_{PE}$ both associated with that new image.

The calculation takes the first dosemeter reading $D_{CAL}$ obtained for the calibration reference exposure as a base value and applies two correction factors to it.

A first correction factor multiplies that dose value with the ratio of the current-time-product post exposure parameters: $ctp_{PE}$ and $ctp_{CAL}$ thus implementing the proportionality of the Exposure=f (CTV) Model.

The second dose correction factor takes the small difference of the tube voltage post exposure parameters: tvPE and tvCAL into account and uses the local gradient $G_{tvCAL}$ calculated from the measured Exposure=f (Tube Voltage) Model.

The generator feedback based dose $D_{GPEP}$ is calculated for each new image using the generator's post exposure parameters in combination with extracted calibration reference data by the formula:

$$D_{GPEP} = D_{CAL} \cdot (ctp_{PE}/ctp_{CAL}) \cdot (1 + G_{tvCAL} \cdot (tV_{PE} - tV_{CAL}))$$

Figure 5:
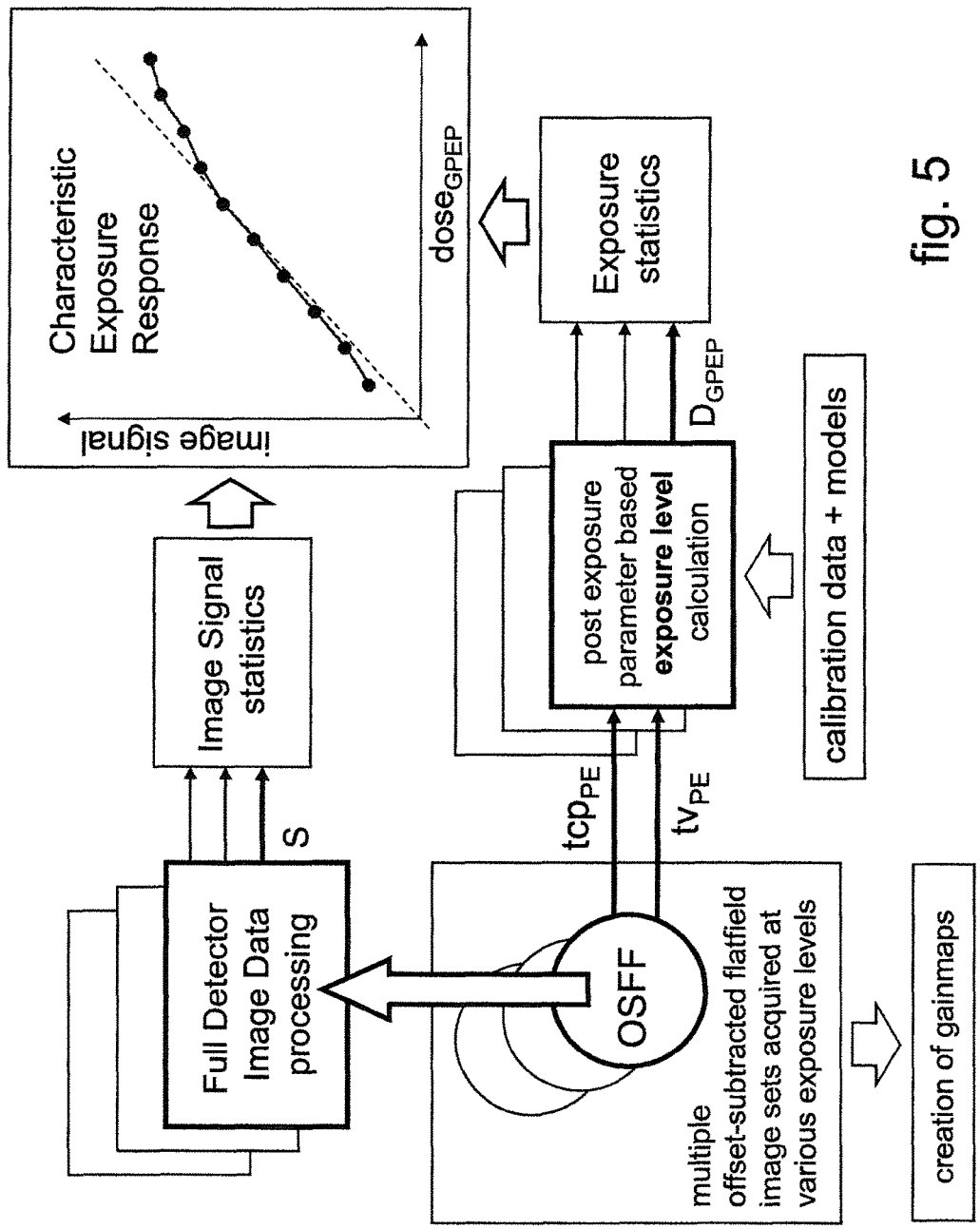
FIG. 5 depicts the extraction of the characteristic exposure response of a radiographic system.

FIG. 5 depicts the extraction of the characteristic exposure response of a radiographic system.

During system calibration multiple image sets composed of evenly exposed flatfield and time-associated unexposed offset images are acquired along with their corresponding post exposure parameters data from the generator at various exposure levels.

The offset-subtracted OSFF images are calculated first by subtracting the offset image from its corresponding flatfield exposed image for each of these image sets.

The OSFF images acquired at the same exposure level are grouped and a gain-map for pixel wise relative sensitivity corrections is calculated for each exposure level.

In addition to this regular system calibration flow a post exposure parameter based calculation of the exposure level representative dose $D_{GPEP}$ associated with each of these offset-subtracted flatfield images is performed using the x-ray generator feedback data and the calibration data and models as explained in FIG. 4.

Applying average or median statistics to the thus obtained $D_{GPEP}$ values for all the OSFF images in an exposure level group results into the creation of a point on the horizontal doseGPEP axis of the chart.

This way multiple characteristic exposure level points can be calculated for the multiple OSFF image sets acquired at the various exposure levels.

The image-wide data of all the pixels within the active area of each OSFF image is also subjected to an average or median signal determination process resulting into an overall signal S.

Applying average or median statistics to these exposure level group related S-values results into a system characteristic point on the vertical image signal axis of the chart.

By associating the thus measured, image data related S-points with their corresponding, exposure level related $dose_{GPEP}$-points the flat panel detector's characteristic exposure response is determined as shown by interconnecting the various points obtained.

That system characteristic response represents the absolute level of the detector's image signal as a function of the impinging exposure level at the entry surface and can deviate from the radiographic system's specified characteristic exposure response imposed by dosimetry and image processing requirements.

Figure 6:
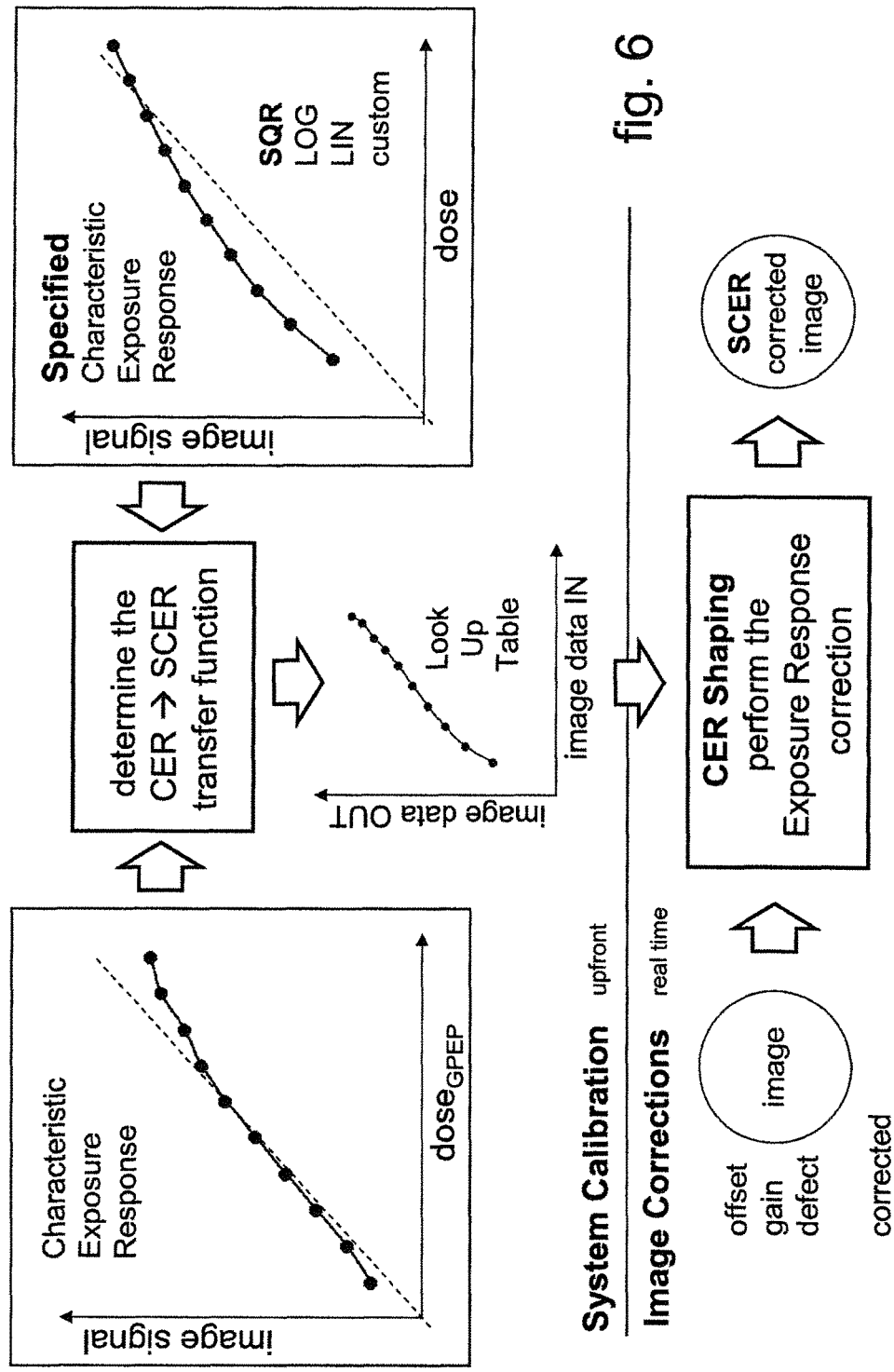
FIG. 6 illustrates how the characteristic exposure response of an offset-, gain- and defect corrected image is reshaped to comply with the specifications.

FIG. 6 explains how the characteristic exposure response of an offset-, gain- and defect corrected image is reshaped to comply with the imposed requirements.

The exemplary represented Specified Characteristic Exposure response refers to a signal level encoding model where the image data is proportional to the square root of the exposure level at the entry surface of the flat panel detector.

Logarithmic, linear or even custom defined responses of the image data to the absorbed dose can also be specified as expected characteristic exposure responses.

During system calibration a transfer function is composed or calculated to convert image signals according to the measured characteristic exposure response into corrected image signals which meet to the expected, specified characteristic exposure response.

This CER→SCER transfer function determines the model of the required signal conversion process as shown in the central graph.

The conversion itself can be implemented by means of a polynomial equation or as an input→output look-up-table data structure.

In normal operation mode the radiographic system acquires a raw diagnostic or inspection image along with its time-associated unexposed offset image.

Both images pass through a long chain of consecutive image corrections which are executed in real time.

First the offset subtracted image is calculated and then the pixel-wise relative sensitivity corrections are applied according to the data available in the various gain-maps.

Defective pixel correction reconstructs the missing or disturbed image pixels, clusters or lines.

Finally an offset, gain and defect image is available at the end of this image correction chain.

The relationship between the image signal and the exposure level is still governed by the system's characteristic exposure response though which can deviate from the expected, specified response.

A characteristic exposure response (CER) shaping or reshaping operation is needed to convert this pre-corrected image into an image which is signal-encoded according to the specified characteristic exposure response and expected dosimetry.

This exposure response correction is performed for each image pixel in the panel's active area by either calculating the value of the transfer function or by using a fast look-up-table. Both methods rely on the transfer model determined upfront during calibration based on a few dose measurements and their related post exposure parameter data from the generator:

$$SCER \text{ image data} = LUT_{CER \to SCER}(CER \text{ image data}).$$

The invention claimed is:

1. A method for reshaping an actual characteristic exposure response of a direct radiography system into a specified exposure response profile, the method comprising the steps of:
    assessing a specified characteristic exposure response;
    determining an actual characteristic exposure response using post exposure parameter data from an x-ray generator of the direct radiography system;
    determining a transfer model to convert image data of the actual characteristic exposure response into corrected image data according to the specified exposure response; and
    converting the image data into the corrected image data using the transfer model; wherein
    a portion of the post exposure parameter data from the x-ray generator relates to dose measurements performed at an entry surface of a flat panel detector of the direct radiography system under reference exposure conditions; and
    the reference exposure conditions include a fixed current-time-product setting at a calibration reference tube voltage for a first exposure and to the same fixed current-time-product setting at a tube voltage that is higher or lower than the calibration reference tube voltage for a second exposure.

2. The method according to claim 1, wherein the step of converting the image data includes pixel-wise applying the transfer model to the image data of the actual characteristic exposure response so as to obtain the corrected image data.

3. The method according to claim 1, wherein a portion of the post exposure parameter data from the x-ray generator relates to evenly x-ray exposed offset-subtracted images acquired at various exposure levels at the calibration reference tube voltage.

4. The method according to claim 3, where a dose based on the post exposure parameter data from the x-ray generator is calculated for the evenly x-ray exposed offset-subtracted images using:
    an image tube voltage and current-time-product post exposure parameters;
    dose measurement and associated post exposure parameters performed at a calibration reference condition; and
    local gradient data derived from an exposure sensitivity to a tube voltage model.

5. The method according to claim 4, further comprising the step of:
    determining a local gradient of the local gradient data based on dose measurements performed under conditions of the first exposure and conditions of the second exposure and on the tube voltage and the fixed current-time-product setting of the first exposure and the second exposure.

6. The method according to claim 5, further comprising the step of:
    assessing the actual characteristic exposure response at various exposure levels by determining a characteristic dose point using average or median statistics on a plurality of calculated post exposure parameter based dose values and by determining a corresponding characteristic image signal point using average or median statistics on individual image signals obtained by averaging image data of all pixels in the evenly x-ray exposed offset-subtracted image.

7. A non-transitory computer readable medium comprising computer executable program code adapted to carry out the steps of the method according to claim 1 when run on a computer.

* * * * *